United States Patent
AlRayaan et al.

(10) Patent No.: US 11,988,091 B2
(45) Date of Patent: May 21, 2024

(54) SUBSURFACE CONTAMINATION SOURCE DETECTION AND TRACKING DEVICE USING ARTIFICIAL INTELLIGENCE

(71) Applicant: Saudi Arabian Oil Company, Dhahran (SA)

(72) Inventors: Mohammed B. AlRayaan, Dammam (SA); Faisal S. Aljar, Al Khobar (SA); Ibrahim A. Alshayqi, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 30 days.

(21) Appl. No.: 17/872,457

(22) Filed: Jul. 25, 2022

(65) Prior Publication Data

US 2024/0026786 A1  Jan. 25, 2024

(51) Int. Cl.
*E21B 49/08* (2006.01)
*E21B 7/26* (2006.01)
(Continued)

(52) U.S. Cl.
CPC ............ *E21B 49/081* (2013.01); *E21B 7/267* (2020.05); *G01N 33/24* (2013.01); *G01S 13/885* (2013.01)

(58) Field of Classification Search
CPC ........ E21B 49/081; E21B 7/267; E21B 47/10; E21B 47/138; E21B 47/07; E21B 41/04;
(Continued)

(56) References Cited

U.S. PATENT DOCUMENTS

| 9,202,362 B2 | 12/2015 | Hyland et al. |
| 9,599,597 B1 | 3/2017 | Steele et al. |
| (Continued) | | |

FOREIGN PATENT DOCUMENTS

| CN | 1328017 | 7/2007 |
| CN | 105511472 | 10/2018 |
| (Continued) | | |

OTHER PUBLICATIONS

Herman et al., "First Results in Automonous Retrieval of Buried Objects," presented at the International Conference on Robotics and Automation, San Diego, California, May 1994, 7 pages.
(Continued)

*Primary Examiner* — Yong-Suk (Philip) Ro
(74) *Attorney, Agent, or Firm* — Fish & Richardson P.C.

(57) ABSTRACT

The present disclosure provides a method including: launching a drone-type device into a subsurface terrain, wherein the drone-type device is configured to navigate the subsurface terrain along a path while searching for a source of one or more pollutants; obtaining, using one or more sampling compartments on the drone-type device, at least one sample along the path as the drone-type device travels in the subsurface terrain; measuring, using one or more sensors on the drone-type device on the drone-type device, concentration levels of the one or more pollutants at corresponding locations along the path where the drone-type device obtains the at least one sample; determining a gradient map of the measured concentration levels in the subsurface terrain surrounding the path taken by the drone-type device; and based on, at least in part, the gradient map, determining whether the source of the one or more pollutants has been located.

20 Claims, 5 Drawing Sheets

(51) Int. Cl.
*G01N 33/24* (2006.01)
*G01S 13/88* (2006.01)

(58) Field of Classification Search
CPC . E21B 47/095; B63G 8/001; B63G 2008/002; B63G 2008/004; B63G 2008/005; G01N 33/24; G01S 13/885
See application file for complete search history.

(56) References Cited

U.S. PATENT DOCUMENTS

| | | | |
|---|---|---|---|
| 10,208,585 B2 | 2/2019 | Surowinski et al. | |
| 10,268,198 B2 | 4/2019 | Mantripragada et al. | |
| 10,696,365 B2* | 6/2020 | Dabbous | B63G 8/001 |
| 11,159,909 B2 | 10/2021 | Anderson | |
| 2020/0063553 A1* | 2/2020 | Zemla | E21B 47/092 |
| 2021/0254456 A1* | 8/2021 | Zemla | E21B 33/068 |
| 2021/0404301 A1 | 12/2021 | AlRayaan | |
| 2022/0090992 A1* | 3/2022 | Mortensen | G01N 1/04 |
| 2023/0025615 A1* | 1/2023 | Zemla | E21B 23/08 |
| 2023/0392498 A1* | 12/2023 | Srivastav | E21B 47/10 |

FOREIGN PATENT DOCUMENTS

| | | |
|---|---|---|
| CN | 112253098 | 1/2021 |
| RU | 2608344 | 1/2017 |

OTHER PUBLICATIONS

International Search Report and Written Opinion in International Appln. No. PCT/US2023/028490, mailed Oct. 10, 2023, 22 pages.

* cited by examiner

SUBSURFACE CONTAMINATION SOURCE DETECTION AND TRACKING DEVICE USING ARTIFICIAL INTELLIGENCE

TECHNICAL FIELD

This disclosure generally relates to contamination identification and groundwater protection.

BACKGROUND

Contamination sources can leak into subsurface, which is often difficult to identify from ground level. Once groundwater is polluted, the contamination can pose risks to human health and aquatic life. For example, groundwater contamination could be very harmful to human health if the same aquifer is used as a source of water. Additionally, vapor intrusion could take place if highly volatile organic compounds are present.

SUMMARY

In one aspect, the present disclosure describes a method for operating a drone-type device, the method including: launching a drone-type device into a subsurface terrain, wherein the drone-type device is configured to navigate the subsurface terrain along a path while searching for a source of one or more pollutants; obtaining, using one or more sampling compartments on the drone-type device, at least one sample along the path as the drone-type device travels in the subsurface terrain; measuring, using one or more sensors on the drone-type device on the drone-type device, concentration levels of the one or more pollutants at corresponding locations along the path where the drone-type device obtains the at least one sample; determining a gradient map of the measured concentration levels in the subsurface terrain surrounding the path taken by the drone-type device; and based on, at least in part, the gradient map, determining whether the source of the one or more pollutants has been located.

Implementations may include one or more of the following features.

The operation of determining whether the source of the one or more pollutants has been located may include: identifying a direction corresponding to an ascending gradient on the determined gradient map; and steering the drone-type device in the identified direction in the subsurface terrain. The ascending gradient may include a gradient where the measured concentration level is more elevated than a previously measured concentration level. The method may include: accessing, from a ground penetrating radar (GPR) on the drone-type device, a map of the subsurface terrain surrounding where the drone-type device is located; and based on, at least in part, the map from the GPR, identifying an underground structure. The method may further include: steering the drone-type device such that the path of the drone-type device does not cross the underground structure.

The method may include: obtaining, using one or more sampling compartments on the drone-type device, at least one additional sample as the drone-type device is steered in the identified direction in the subsurface terrain; and measuring, using one or more sensors on the drone-type device on the drone-type device, the concentration levels of the one or more pollutants where the drone-type device obtains the at least one additional sample. The operation of determining whether the source of the one or more pollutants has been located further may include: determining that an ascending gradient is absent where the drone-type device is located; and identifying the source of the one or more pollutants as where the drone-type device is located.

The operation of launching the drone-type device into the subsurface terrain includes at least one of: injecting the drone-type device into an aquifer through the groundwater monitoring well; or injecting the drone-type device into a vadose zone of the aquifer through a driller. The operation of measuring the concentration levels may include: operating at least one of: a pressure gauge, a thermometer, a PH meter, an oxidation-reduction potential (ORP) sensor, a dissolved oxygen (DO) sensor, or a radiation sensor. The method may further include: communicating, using a radio frequency (RF) transceiver system on the drone-type device, data encoding the measured concentration levels to a ground station.

In another aspect, some implementations provide a drone-type device that includes: a driller configured to penetrate media layers in a subsurface terrain such that the drone-type device travels along a path in the subsurface terrain while searching for a source of one or more pollutants; one or more sampling compartments configured to hold at least one sample obtained along the path as the drone-type device travels in the subsurface terrain; one or more sensors on the drone-type device coupled to the one or more sampling compartments, wherein the one or more sensors are configured to measure concentration levels of the one or more pollutants at corresponding locations along the path where the drone-type device obtains the at least one sample; a processor coupled to the one or more sensors, wherein the processor is configured to perform operations of: determining a gradient map of the measured concentration levels in the subsurface terrain surrounding the path taken by the drone-type device; and based on, at least in part, the gradient map, determining whether the source of the one or more pollutants has been located; and a battery coupled to the driller, the one or more sensors, and the processor.

Implementations may include one or more of the following features.

The operation of determining whether the source of the one or more pollutants has been located may include: identifying a direction corresponding to an ascending gradient on the determined gradient map; and steering the drone-type device in the identified direction in the subsurface terrain. The ascending gradient may include a gradient where the measured concentration level is more elevated than a previously measured concentration level.

The drone-type device may further include: a ground penetrating radar (GPR) configured to generate a map of the subsurface terrain surrounding where the drone-type device is located. The processor may be further configured to perform operations of: accessing the map of the subsurface terrain; and based on, at least in part, the map, identifying an underground structure. The processor may be further configured to perform operations of: steering the drone-type device such that the path of the drone-type device does not cross the underground structure.

The drone-type device may be further configured to: obtain, using the one or more sampling compartments, at least one additional sample as the drone-type device is steered in the identified direction in the subsurface terrain; and measure, using the one or more sensors, the concentration levels of the one or more pollutants where the drone-type device obtains the at least one additional sample. The operation of determining whether the source of the one or more pollutants has been located may further include:

determining that an ascending gradient is absent where the drone-type device is located; and identifying the source of the one or more pollutants as where the drone-type device is located.

The one or more sensors may further include at least one of: a pressure gauge, a thermometer, a PH meter, an oxidation-reduction potential (ORP) sensor, a dissolved oxygen (DO) sensor, or a radiation sensor. The drone-type device may further include: a radio frequency (RF) transceiver system configured to communicate data encoding the measured concentration levels to a ground station. The radio frequency (RF) transceiver system may be further configured to receive at least one command from ground station such that the one or more sampling compartments are opened according to the at least one command.

Implementations according to the present disclosure may be realized in computer implemented methods, hardware computing systems, and tangible computer readable media. For example, a system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

The details of one or more implementations of the subject matter of this specification are set forth in the description, the claims, and the accompanying drawings. Other features, aspects, and advantages of the subject matter will become apparent from the description, the claims, and the accompanying drawings.

DESCRIPTION OF DRAWINGS

Like reference numbers and designations in the various drawings indicate like elements.

DETAILED DESCRIPTION

The technology relates to a drone-type device capable of travelling through the subsurface medium to detect and track contamination sources. The drone-type device can be battery powered and equipped with a global positioning system (GPS), a ground penetrating radar (GPR), and sensors. The sensors can accurately measure the pollutants' concentrations as the drone device travels through the subsurface. By analyzing a gradient map of concentration levels of a contaminant, the drone-type device can ultimately locate the contamination source. Once the contamination source is located, the device can be then retrieved for cleaning and calibration before being launched again for another survey. In some configurations, the device can be fitted with sampling compartments to take groundwater sample and allow users to check in-situ in addition to off-line lab test that analyzes the samples for accurate identification of pollutant. The device can thus detect and track contamination dispersion through a subsurface terrain with high accuracy.

Currently, contamination sources that leak pollutants into a subsurface terrain to reach groundwater. The leakage processes are often difficult to identify from the ground level. For example, several potential sources of contamination may be present concurrently, which is usually the case in oil and gas production plants. To address contamination, environmental protection agencies often utilize groundwater wells to collect groundwater samples, analyze the collected samples in a lab, and then identify pollution at different subsurface levels. This approach is considered as "after the fact," meaning that contamination has already reached groundwater, thereby leaving little room for earlier intervention that could have prevented or minimized groundwater contamination. Once groundwater has been polluted, its quality will degrade and its accessibility must be restricted. Groundwater contamination can pose risks to human health and the general environment including aquatic life. In addition, groundwater contamination could be very harmful to human health if the same aquifer is utilized as a source of water and vapor intrusion could take place if highly volatile organic compounds are present.

Figure 1:
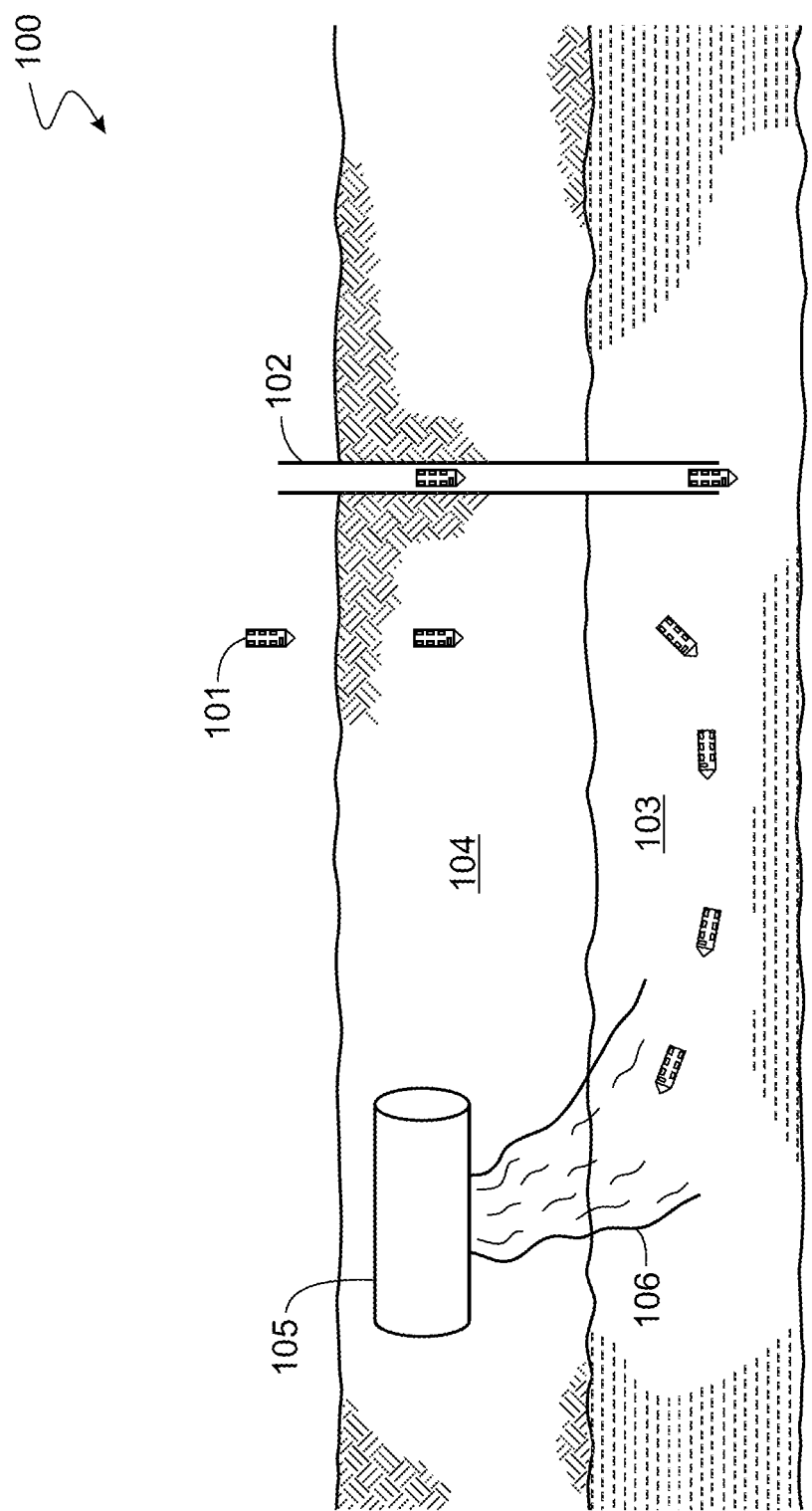
FIG. 1 is diagram illustrating an example of operating a drone-type device according to an implementation of the present disclosure.

Referring to FIG. 1, some implementations incorporate a drone-type device to navigate the subsurface terrain for identifying contamination sources as early as possible so that the early alarm can allow actions to be taken that can effectively prevent the contamination from reaching groundwater, thereby avoiding difficult and time-consuming cleanup. Detecting the source of contamination before the contaminants reach groundwater can be a significant factor in avoiding unnecessary remediation efforts which tend to be very costly and time consuming.

As illustrated in diagram 100, the drone-type device 101 can autonomously navigate the subsurface terrain to search for signs of contamination and trace the contamination back to a source. The drone-type device 101 can be deployed from the entrance to a groundwater well 102. Additionally or alternatively, the drone-type device 101 can be deployed from the top surface. In various implementations, the drone-type device 101 can descend to reach shallow groundwater (up to 25 m) 103. The drone-type device 101 may navigate in groundwater 103, for example, in an upstream fashion.

Figure 2:
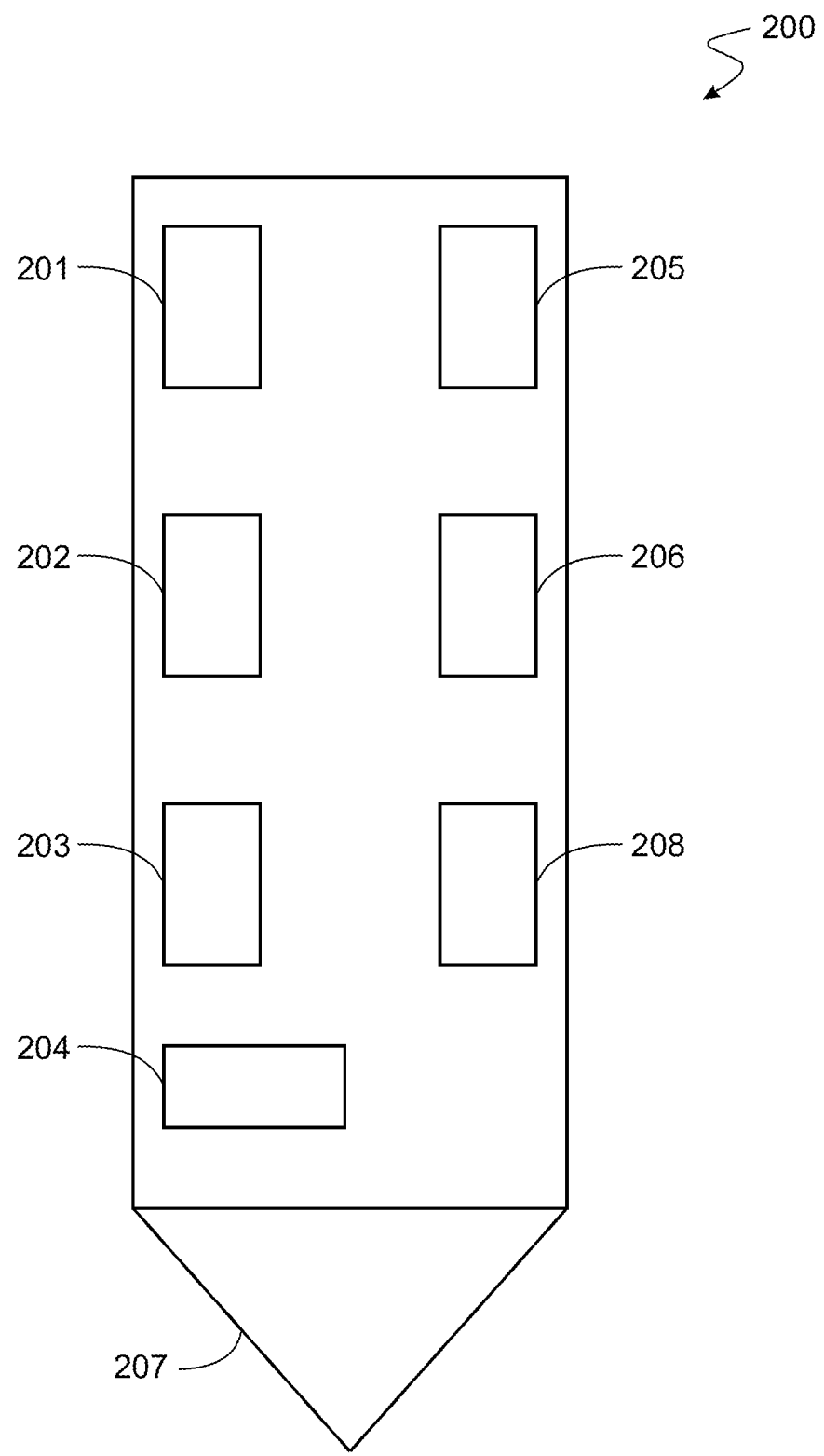
FIG. 2 illustrates an example of a drone-type device according to some implementations of the present disclosure.

Further referring to FIG. 2, the drone-type device 101 may include a battery 201, one or more compartments 202, a global positioning system (GPS) receiver 203, a ground penetrating radar (GPR) 204, a radio-frequency (RE) transceiver system 205, a driller 206, and an intelligent system 207. The drone-type device 101 may additionally incorporate one or more sensors 208 such as a pressure gauge, a thermometer, a PH meter, an oxidation-reduction potential (ORP) sensor, a dissolved oxygen (DO) sensor, or a radiation sensor (e.g., a Geiger counter). In some cases, sensors 208 can measure the concentration levels in ppm in a specified travel distance moving from low concentrations to higher concentrations. The driller 206 can penetrate the media before the drone-type device 101 and allow the drone-type device 101 to travel through the subsurface media.

Battery 201 can include a lithium ion battery, a sodium ion battery, or a solid state battery. The one or more compartments 202 may hold sampled water or soil. For example, the drone-type device 101 may incorporate mechanical arms to excavate water or soil samples from the surroundings into the one or more compartments 202. The one or more compartments can be remotely opened so that samples of the subsurface groundwater or core can be loaded. For groundwater sampling, the compartments can include filters to remove soil and sands to allow for liquid-only media. The drone-type device 101 may then, using one or more sensors 208, to measure, for example, a subsurface characteristic (including, for example, porosity, flowrate, hydraulic conductivity, soil types, ... etc.). The one or more sensors 208 may also measure a concentration level of a substance in the held sample.

As illustrated, the drone-type device 101 includes driller 206 capable of penetrating; soil 104 until the drone-type device 101 reaches groundwater 103. Because soil 104, as a media layer/surrounding, is not fully porous, the drone-type device 101 employs driller 206 to cut a path so that the drone-type device 101 can travel through the subsurface media (including e.g., soil, sands, gravel) to track and locate the contamination source 105. For example, when the drone-type device 101 reaches groundwater 103, the drone-type device 101 can migrate and track the source of contamination 105 by following a measured gradient of pollutant's concentration, which is indicative of local diffusion and dispersion patterns of the pollutants. The local diffusion and dispersion patterns are illustrated as pattern 106 leaking from contamination source 105 into groundwater 103.

In some cases, the drone-type device can be submersed in the vadose zone of the aquifer through driller. In other cases, the drone-type device 101 can be injected into the aquifer through the groundwater monitoring well. For example, the drone-type device 101 can be injected into the subsurface using a tethering cable that connects, for example, a back-end of the drone-type device 101 to an anchoring station. The tethering cable may provide mechanical connection, electrical power, as well as data communication. Alternatively or additionally, the drone-type device 101 can launched through an existing groundwater monitoring well. Various implementations may employ ground penetrating radar (GPR) 204 to survey the area so that the drone-type device 101 can navigate around underground cables, and existing pipelines.

Importantly, the drone-type device 101 can incorporate an artificial intelligence (AI) system 207 for autonomous navigation, for example, to trace the source of a contamination by following a path towards a higher concentration of pollutants. In some implementations, as the drone-type device 101 travels through the subsurface, the RF transceiver system 205 can report the position, as recorded by GPS receiver 203, along with, for example, the measured concentration at the location to a user terminal of an operator on the ground. In some cases, the drone-type device 101 may communicate with an anchoring station on the ground through a wired channel inside a tethering cable. In one illustration, the wired channel may accommodate an optical fiber.

The drone-type device 101 may analyze concentration levels and then navigate towards higher concentrations of pollutants, thereby leading to more accurate localization of the source of the pollution. In some cases, the drone-like device 101 may record measured concentration levels along the path, and calculate a spatial gradient of the measured concentration levels. The gradient can be computed as a difference in measured concentration levels at two distinct spatial positions. Using the AI system 207, the drone-like device 101 may determine a route in a direction that ascends the computed spatial gradient and towards the location corresponding to heightened concentration levels. For example, the AI system 207 may have a pre-installed data structure that maps measured concentration levels as a function of spatial coordinates to a corresponding direction to navigate. The data structure may be generated based on past records for taking a particular direction or turn when presented with the spatial distributions of measured concentration levels. The data structure can be built based on past records and through AI training process that involves artificial neural networks (ANNs) with multiple layers. Using this data structure, the AI-system 207 can efficiently compute a direction/turn to take when seeing a given spatial pattern of measured concentration levels. In this manner, the drone-like device 101 can navigate upstream towards to source of the contamination where the concentration level tends to be the highest. Once the contaminant source is located, the drone-type device 101 can be then retrieved. For example, the drone-type device 101 can back-track the incoming path to return to the launch site. Once the drone-type device 101 is retrieved, the operator may perform cleaning and calibration procedures. For example, the samples held in the one or more compartments 202 may be analyzed in a lab and the lab readings may be compared with those measurements taken on-site. The comparison may provide calibration of the on-board meters. Once cleaned and calibrated, the drone-type device 101 may be launched for another surveillance mission.

Using the one or more compartments 202, the drone-type device 101 can sample on-demand along its path at any depth or interval. Consequently, the drone-type device 101 can replace conventional "nested wells" used to collect samples at intervals and depths that are constrained by the geometry of the nested wells drilled at fixed locations in the field.

The device can thus serve as a robust and accurate pollution identification and tracking tool. This tool can effectively mitigate risks of pollution, reduce cost of operation and maintenance, and support remediation efforts after a contamination source has been identified. In comparison, conventional methods cannot accurately and timely locate the source of contamination especially in the presence of several concurrent potential sources. The occurrence of concurrent sources is frequent in every operating facility. Consequently, the complexity has plagued the oil and gas industry for some time. In one example, conventional approaches require drilling several groundwater monitoring wells in order to assess the quality of the groundwater and characterize the lithology of the subsurface. The configuration also entails inspecting all potential sources of contamination including manholes, or sump pits. The overhead of drilling and inspection generally require large sums of investment in terms of money and time. The drone-type device 101 can not only save up to $300 K per facility, but can also overcome the deficiencies and shortcomings of conventional methods, thereby enabling users to identify the contaminants and the corresponding sources within a reasonable period of time and with high accuracy. In various implementations, sensors on the drone-type device 101 are modular and can be replaceable. For example, the sensors (e.g., PH meter) can be installed based on the type of the underlying pollutants (e.g., chemical, radioactive substances) and subsurface medium.

Figure 3:
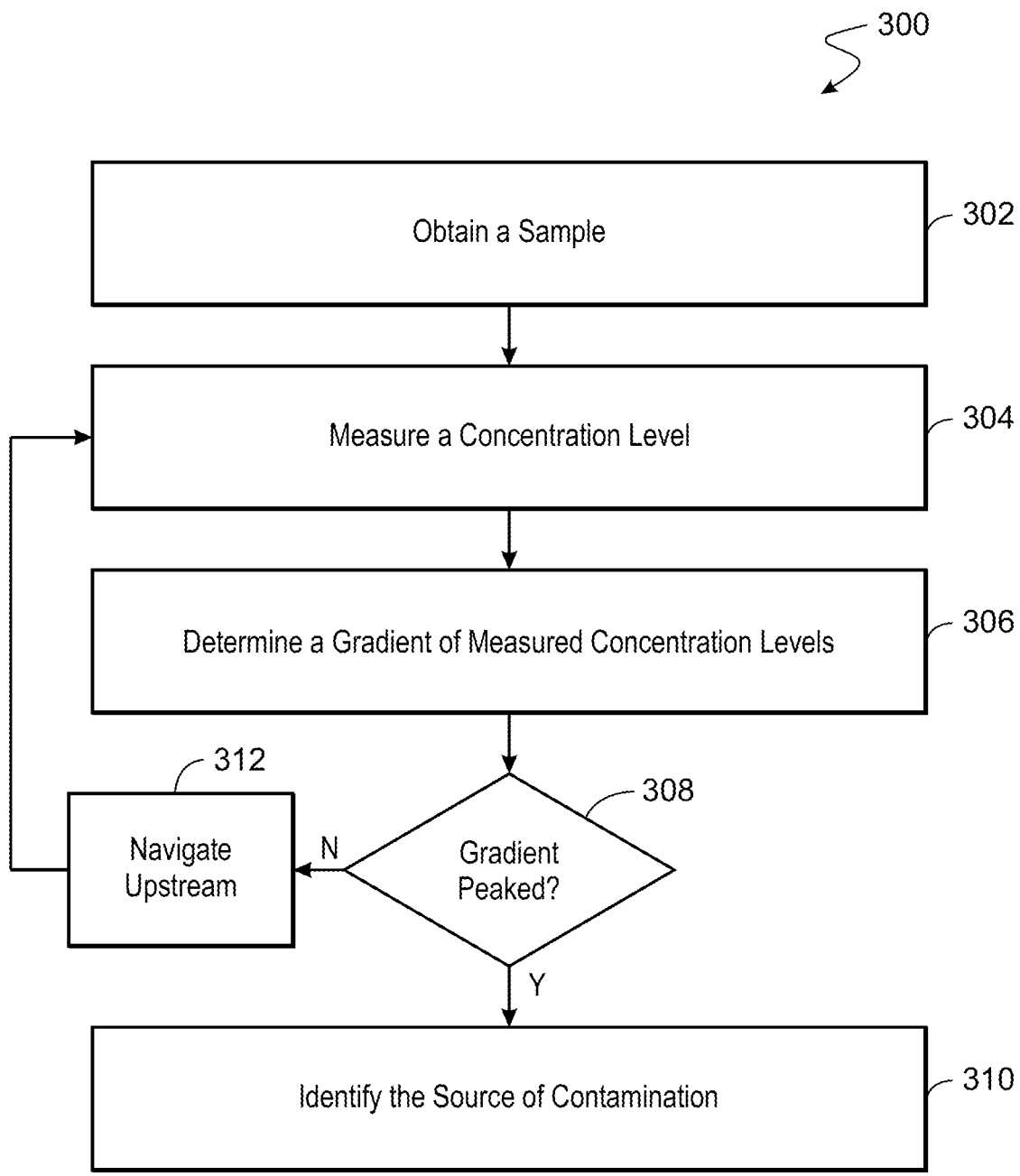
FIG. 3 illustrates a flow chart of an example of a process according to some implementations of the present disclosure.

Further referring to FIG. 3, a flow chart illustrates an example of a process 300 according to some implementations. Initially, process 300 may start with releasing a drone-type device 101 into the subsurface terrain. In some cases, drone-type device 101 can be injected into the subsurface using a tethering cable. In some cases, the drone-type device 101 can also be injected into the aquifer through the groundwater monitoring well. The drone-type device 101 may incorporate ground penetrating radar (GPR) 204 for surveying the surrounding area to navigate around underground cables, and existing pipelines. The drone-type device 101 may include one or more compartments 202 so that a sample of the surrounding subsurface groundwater or core can be obtained (302).

Process 300 may then proceed to measure a concentration level of a substance in the obtained sample (304). As illustrated in FIGS. 1 and 2, the drone-type device 101 may include one or more sensors 208 to measure the concentration level. Examples of a sensor can include a pressure gauge, a thermometer, a PH meter, an oxidation-reduction potential (ORP) sensor, a dissolved oxygen (DO) sensor, or a radiation sensor (e.g., a Geiger counter).

By measuring the concentration level at a number of spatial positions in the subsurface, a gradient of the measured concentration levels may be obtained (306). As discussed above in association with FIGS. 1 and 2, the gradient may be computed as the difference between the measured concentration levels at two distinct spatial locations. Indeed, a spatial distribution of the gradient may be obtained.

Process 300 may then determine whether the gradient at a particular location has peaked (308). As discussed above in association with FIGS. 1 and 2, the implementations may identify a direction corresponding to the most ascending gradient, which points to the preferred direction for navigating the drone-type device 101. The preferred direction can be used to navigate the drone-type device 101 upstream towards the source of the pollution (312), except when the preferred direction conflicts with existing buried pipes or other obstacles. When the preferred direction is blocked, the runner-up direction for an ascending gradient can be used. Once the drone-type device 101 is navigated upstream, process 300 may repeat the measuring step 304 and the determining step 306 until a gradient peak has been identified. Here, a gradient peak is identified where no ascending gradient can be found, i.e., the gradient map shows descending patterns in all directions. When this happens, the process may identify the location as the source of contaminants (310).

Figure 4:
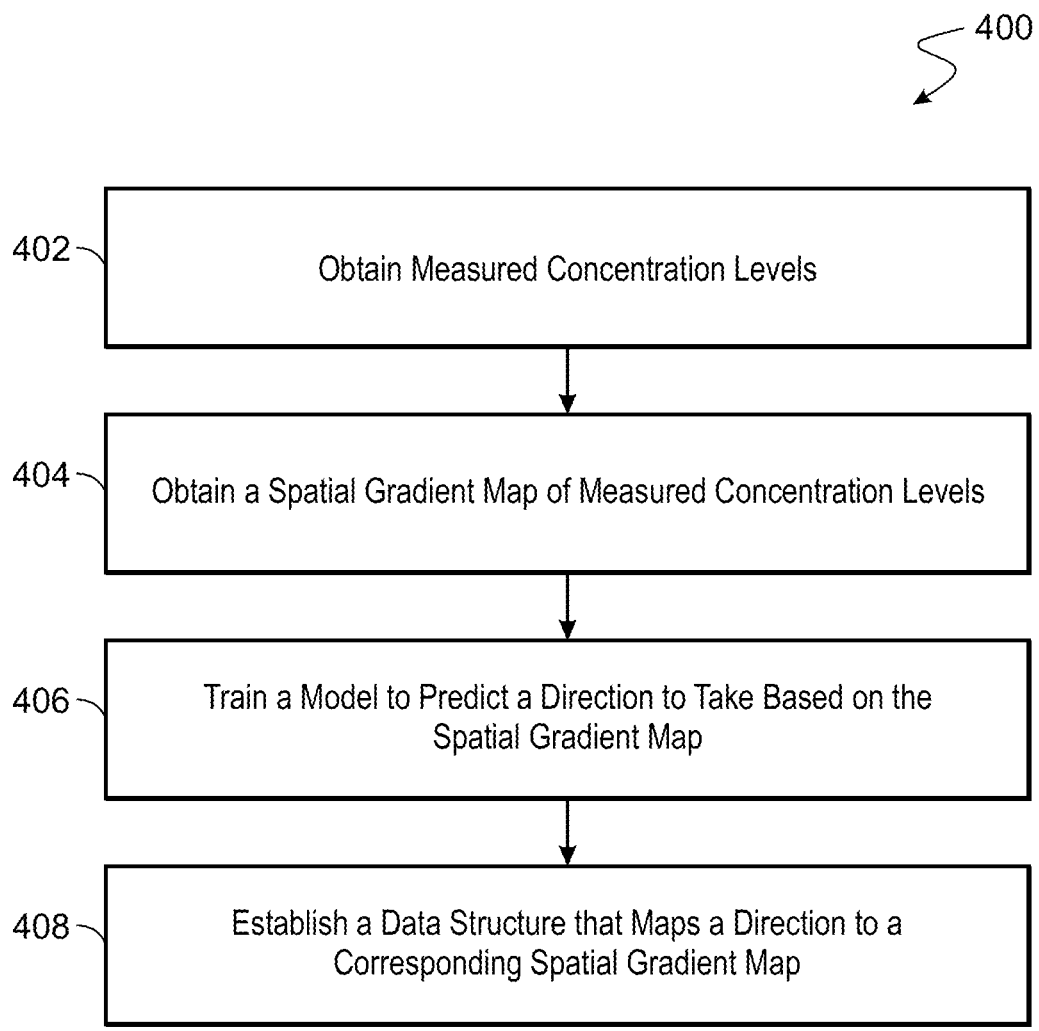
FIG. 4 illustrates a flow chart of another example of a process according to some implementations of the present disclosure.
Figure 5:
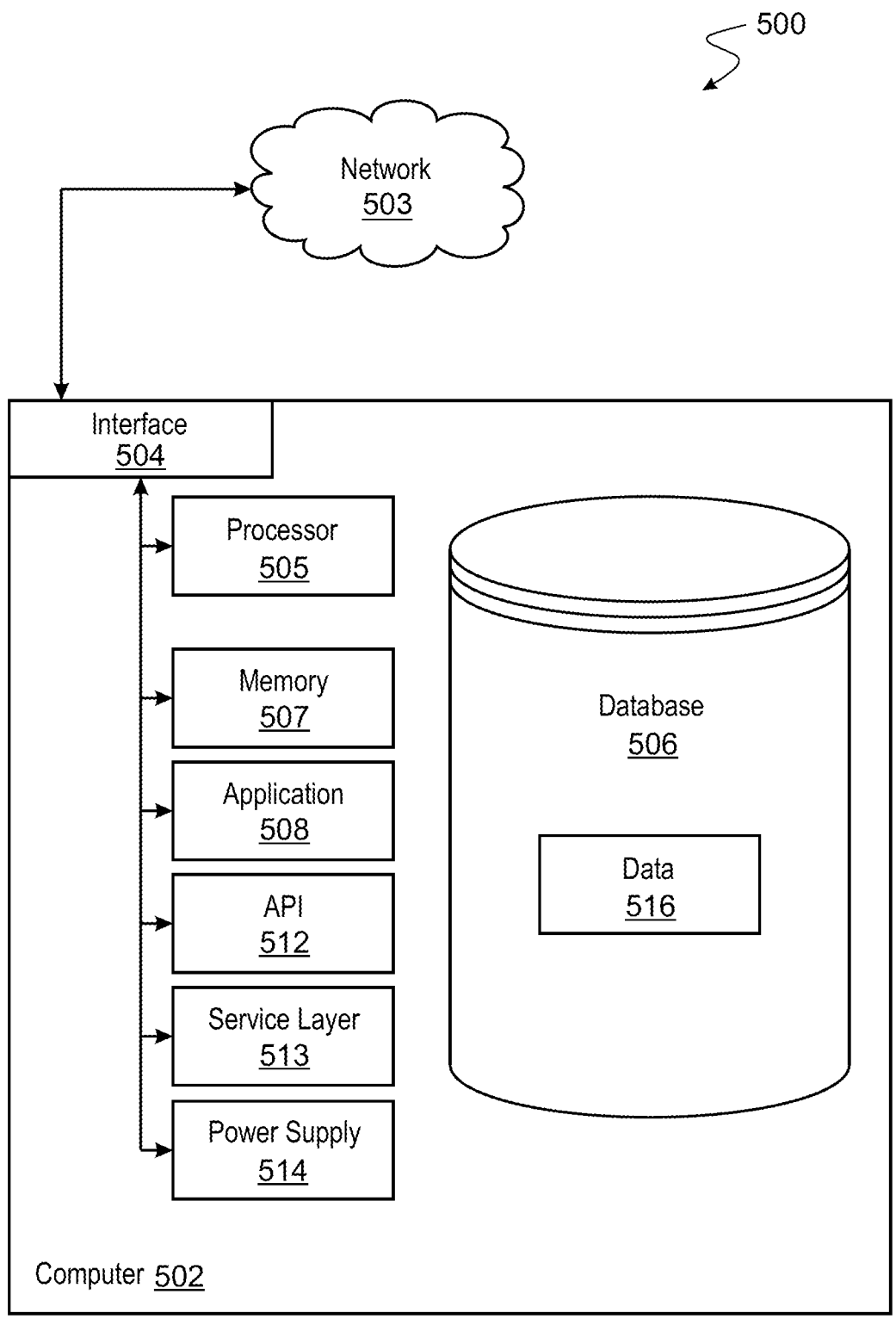
FIG. 5 is a block diagram illustrating an example of a computer system used to provide computational functionalities associated with described algorithms, methods, functions, processes, flows, and procedures, according to an implementation of the present disclosure.

Further referring to FIG. 4, a flow chart illustrates an example of a process 400 in which an AI model is being trained according to some implementations. Process 400 may start with obtaining measured concentration levels at various and distinct subsurface locations (402). Process 400 may then obtain a spatial gradient map of measured concentration levels (404). The gradient map may cover the vicinity of a particular location, e.g., within 500 feet of a coordinate. Process 400 may then train a model to predict a direction to take based on the spatial gradient map (406). The training can start with seed values for the predicted direction based on an initial gradient map. The training may then build an AI model that identifies the specific direction based on a corresponding gradient map, along with a radar map of the surrounding (e.g., mapping obtained from GPR 204). In other words, the learning process may train an AI model that identifies, when given a specific gradient map, the most likely direction for navigating the drone-type device 101. The training can involve multiple layers of artificial neural networks (ANNs). Once the AI model has been trained, process 400 stores a data structure that encodes a mapping from a gradient map to a navigation direction. Based on this mapping, a direction can be obtained by a simple look-up operation, FIG. 5 is a block diagram illustrating an example of a computer system 500 used to provide computational functionalities associated with described algorithms, methods, functions, processes, flows, and procedures, according to an implementation of the present disclosure. For example, the computer system 500 may implement the AI system 207 onboard drone-type device 101. The computer system 500 may also implement model training as illustrated in, for example, FIG. 4. The illustrated computer 502 is intended to encompass any computing device such as a server, desktop computer, laptop/notebook computer, wireless data port, smart phone, personal data assistant (PDA), tablet computing device, one or more processors within these devices, another computing device, or a combination of computing devices, including physical or virtual instances of the computing device, or a combination of physical or virtual instances of the computing device. Additionally, the computer 502 can comprise a computer that includes an input device, such as a keypad, keyboard, touch screen, another input device, or a combination of input devices that can accept user information, and an output device that conveys information associated with the operation of the computer 502, including digital data, visual, audio, another type of information, or a combination of types of information, on a graphical-type user interface (UI) (or GUI) or other UI.

The computer 502 can serve in a role in a computer system as a client, network component, a server, a database or another persistency, another role, or a combination of roles for performing the subject matter described in the present disclosure. The illustrated computer 502 is communicably coupled with a network 503. In some implementations, one or more components of the computer 502 can be configured to operate within an environment, including cloud-computing-based, local, global, another environment, or a combination of environments.

The computer 502 is an electronic computing device operable to receive, transmit, process, store, or manage data and information associated with the described subject matter. According to some implementations, the computer 502 can also include or be communicably coupled with a server, including an application server, e-mail server, web server, caching server, streaming data server, another server, or a combination of servers.

The computer 502 can receive requests over network 503 (for example, from a client software application executing on another computer 502) and respond to the received requests by processing the received requests using a software application or a combination of software applications. In addition, requests can also be sent to the computer 502 from internal users, external or third-parties, or other entities, individuals, systems, or computers.

Each of the components of the computer 502 can communicate using a system bus 503. In some implementations, any or all of the components of the computer 502, including hardware, software, or a combination of hardware and software, can interface over the system bus 503 using an application programming interface (API) 512, a service layer 513, or a combination of the API 512 and service layer 513. The API 512 can include specifications for routines, data structures, and object classes. The API 512 can be either computer-language independent or dependent and refer to a complete interface, a single function, or even a set of APIs.

The service layer 513 provides software services to the computer 502 or other components (whether illustrated or not) that are communicably coupled to the computer 502. The functionality of the computer 502 can be accessible for all service consumers using this service layer. Software services, such as those provided by the service layer 513, provide reusable, defined functionalities through a defined interface. For example, the interface can be software written in JAVA, C++, another computing language, or a combination of computing languages providing data in extensible markup language (XML) format, another format, or a combination of formats. While illustrated as an integrated component of the computer 502, alternative implementations can illustrate the API 512 or the service layer 513 as stand-alone components in relation to other components of the computer 502 or other components (whether illustrated or not) that are communicably coupled to the computer 502. Moreover, any or all parts of the API 512 or the service layer 513 can be implemented as a child or a sub-module of another software module, enterprise application, or hardware module without departing from the scope of the present disclosure.

The computer 502 includes an interface 504. Although illustrated as a single interface 504 in FIG. 5, two or more interfaces 504 can be used according to particular needs, desires, or particular implementations of the computer 502. The interface 504 is used by the computer 502 for communicating with another computing system (whether illustrated or not) that is communicatively linked to the network 503 in a distributed environment. Generally, the interface 504 is operable to communicate with the network 503 and comprises logic encoded in software, hardware, or a combination of software and hardware. More specifically, the interface 504 can comprise software supporting one or more communication protocols associated with communications such that the network 503 or interface's hardware is operable to communicate physical signals within and outside of the illustrated computer 502.

The computer 502 includes a processor 505. Although illustrated as a single processor 505 in FIG. 5, two or more processors can be used according to particular needs, desires, or particular implementations of the computer 502. Generally, the processor 505 executes instructions and manipulates data to perform the operations of the computer 502 and any algorithms, methods, functions, processes, flows, and procedures as described in the present disclosure.

The computer 502 also includes a database 506 that can hold data for the computer 502, another component communicatively linked to the network 503 (whether illustrated or not), or a combination of the computer 502 and another component. For example, database 506 can be an in-memory, conventional, or another type of database storing data consistent with the present disclosure. In some implementations, database 506 can be a combination of two or more different database types (for example, a hybrid in-memory and conventional database) according to particular needs, desires, or particular implementations of the computer 502 and the described functionality. Although illustrated as a single database 506 in FIG. 5, two or more databases of similar or differing types can be used according to particular needs, desires, or particular implementations of the computer 502 and the described functionality. While database 506 is illustrated as an integral component of the computer 502, in alternative implementations, database 506 can be external to the computer 502. As illustrated, the database 506 holds the previously described data 516 including, for example, data encoding the measured concentration levels, the gradient map of concentration levels, and the path or trajectory taken by the drone-type device 101.

The computer 502 also includes a memory 507 that can hold data for the computer 502, another component or components communicatively linked to the network 503 (whether illustrated or not), or a combination of the computer 502 and another component. Memory 507 can store any data consistent with the present disclosure. In some implementations, memory 507 can be a combination of two or more different types of memory (for example, a combination of semiconductor and magnetic storage) according to particular needs, desires, or particular implementations of the computer 502 and the described functionality. Although illustrated as a single memory 507 in FIG. 5, two or more memories 507 or similar or differing types can be used according to particular needs, desires, or particular implementations of the computer 502 and the described functionality. While memory 507 is illustrated as an integral component of the computer 502, in alternative implementations, memory 507 can be external to the computer 502.

The application 508 is an algorithmic software engine providing functionality according to particular needs, desires, or particular implementations of the computer 502, particularly with respect to functionality described in the present disclosure. For example, application 508 can serve as one or more components, modules, or applications. Further, although illustrated as a single application 508, the application 508 can be implemented as multiple applications 508 on the computer 502. In addition, although illustrated as integral to the computer 502, in alternative implementations, the application 508 can be external to the computer 502.

The computer 502 can also include a power supply 514. The power supply 514 can include a rechargeable or non-rechargeable battery that can be configured to be either user- or non-user-replaceable. In some implementations, the power supply 514 can include power-conversion or management circuits (including recharging, standby, or another power management functionality). In some implementations, the power-supply 514 can include a power plug to allow the computer 502 to be plugged into a wall socket or another power source to, for example, power the computer 502 or recharge a rechargeable battery.

There can be any number of computers 502 associated with, or external to, a computer system containing computer 502, each computer 502 communicating over network 503. Further, the term "client," "user," or other appropriate terminology can be used interchangeably, as appropriate, without departing from the scope of the present disclosure. Moreover, the present disclosure contemplates that many users can use one computer 502, or that one user can use multiple computers 502.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal, for example, a machine-generated electrical, optical, or electromagnetic signal that is generated to encode information for transmission to a receiver apparatus for execution by a data processing apparatus. The computer-storage medium can be a machine-readable storage device, a machine-readable storage substrate, a random or serial access memory device, or a combination of computer-storage mediums. Configuring one or more computers means that the one or more computers have installed hardware, firmware, or software (or combinations of hardware, firmware, and software) so that when the software is executed by the one or more computers, particular computing operations are performed.

The term "real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access the data can be less than 1 millisecond (ms), less than 1 second (s), or less than 5 s. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include special purpose logic circuitry, for example, a central processing unit (CPU), an FPGA (field programmable gate array), or an ASIC (application-specific integrated circuit). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with an operating system of some type, for example LINUX, UNIX, WINDOWS, MAC OS, ANDROID, IOS, another operating system, or a combination of operating systems.

A computer program, which can also be referred to or described as a program, software, a software application, a unit, a module, a software module, a script, code, or other component can be written in any form of programming language, including compiled or interpreted languages, or declarative or procedural languages, and it can be deployed in any form, including, for example, as a stand-alone program, module, component, or subroutine, for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network.

While portions of the programs illustrated in the various figures can be illustrated as individual components, such as units or modules, that implement described features and functionality using various objects, methods, or other processes, the programs can instead include a number of sub-units, sub-modules, third-party services, components, libraries, and other components, as appropriate. Conversely, the features and functionality of various components can be combined into single components, as appropriate. Thresholds used to make computational determinations can be statically, dynamically, or both statically and dynamically determined.

Described methods, processes, or logic flows represent one or more examples of functionality consistent with the present disclosure and are not intended to limit the disclosure to the described or illustrated implementations, but to be accorded the widest scope consistent with described principles and features. The described methods, processes, or logic flows can be performed by one or more programmable computers executing one or more computer programs to perform functions by operating on input data and generating output data. The methods, processes, or logic flows can also be performed by, and apparatus can also be implemented as, special purpose logic circuitry, for example, a CPU, an FPGA, or an ASIC.

Computers for the execution of a computer program can be based on general or special purpose microprocessors, both, or another type of CPU. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable memory storage device.

Non-transitory computer-readable media for storing computer program instructions and data can include all forms of media and memory devices, magnetic devices, magneto optical disks, and optical memory device. Memory devices include semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Magnetic devices include, for example, tape, cartridges, cassettes, internal/removable disks. Optical memory devices include, for example, digital video disc (DVD), CD-ROM, DVD+/-R, DVD-RAM, DVD-ROM, HD-DVD, and BLURAY, and other optical memory technologies. The memory can store various objects or data, including caches, classes, frameworks, applications, modules, backup data, jobs, web pages, web page templates, data structures, database tables, repositories storing dynamic information, or other appropriate information including any parameters, variables, algorithms, instructions, rules, constraints, or references. Additionally, the memory can include other appropriate data, such as logs, policies, security or access data, or reporting files. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input can also be provided to the computer using a touchscreen, such as a tablet computer surface with pressure sensitivity, a multi-touch screen using capacitive or electric sensing, or another type of touchscreen. Other types of devices can be used to interact with the user. For example, feedback provided to the user can be any form of sensory feedback. Input from the user can be received in any form, including acoustic, speech, or tactile input. In addition, a computer can interact with the user by sending documents to and receiving documents from a client computing device that is used by the user.

The term "graphical user interface," or "GUI," can be used in the singular or the plural to describe one or more graphical user interfaces and each of the displays of a particular graphical user interface. Therefore, a GUI can represent any graphical user interface, including but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 or other protocols consistent with the present disclosure), all or a portion of the Internet, another communication network, or a combination of communication networks. The communication network can communicate with, for example, Internet Protocol (IP) packets, Frame Relay frames, Asynchronous Transfer Mode (ATM) cells, voice, video, data, or other information between networks addresses.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what can be claimed, but rather as descriptions of features that can be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features can be described as acting in certain combinations and even initially claimed as such, one or more features from a claimed combination can, in some cases, be excised from the combination, and the claimed combination can be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations can be considered optional), to achieve desirable results. In certain circumstances, multitasking or parallel processing (or a combination of multitasking and parallel processing) can be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A method for operating a drone-type device, the method comprising:
    launching a drone-type device into a subsurface terrain, wherein the drone-type device is configured to navigate the subsurface terrain along a path while searching for a source of one or more pollutants;
    obtaining, using one or more sampling compartments on the drone-type device, at least one sample along the path as the drone-type device travels in the subsurface terrain;
    measuring, using one or more sensors on the drone-type device on the drone-type device, concentration levels of the one or more pollutants at corresponding locations along the path where the drone-type device obtains the at least one sample;
    determining a gradient map of the measured concentration levels in the subsurface terrain surrounding the path taken by the drone-type device; and based on, at least in part, the gradient map, determining whether the source of the one or more pollutants has been located.

2. The method of claim 1, wherein determining whether the source of the one or more pollutants has been located comprises:
identifying a direction corresponding to an ascending gradient on the determined gradient map; and
steering the drone-type device in the identified direction in the subsurface terrain.

3. The method of claim 2, wherein the ascending gradient comprises a gradient where the measured concentration level is more elevated than a previously measured concentration level.

4. The method of claim 2, further comprising:
accessing, from a ground penetrating radar (GPR) on the drone-type device, a map of the subsurface terrain surrounding where the drone-type device is located; and
based on, at least in part, the map from the GPR, identifying an underground structure.

5. The method of claim 4, further comprising:
steering the drone-type device such that the path of the drone-type device does not cross the underground structure.

6. The method of claim 2, further comprising:
obtaining, using one or more sampling compartments on the drone-type device, at least one additional sample as the drone-type device is steered in the identified direction in the subsurface terrain; and
measuring, using one or more sensors on the drone-type device on the drone-type device, the concentration levels of the one or more pollutants where the drone-type device obtains the at least one additional sample.

7. The method of claim 2, wherein determining whether the source of the one or more pollutants has been located further comprises:
determining that an ascending gradient is absent where the drone-type device is located; and
identifying the source of the one or more pollutants as where the drone-type device is located.

8. The method of claim 1, wherein launching the drone-type device into the subsurface terrain comprises at least one of:
injecting the drone-type device into an aquifer through a groundwater monitoring well; or
injecting the drone-type device into a vadose zone of the aquifer through a driller.

9. The method of claim 1, wherein measuring the concentration levels comprises:
operating at least one of: a pressure gauge, a thermometer, a PH meter, an oxidation-reduction potential (ORP) sensor, a dissolved oxygen (DO) sensor, or a radiation sensor.

10. The method of claim 1, further comprising:
communicating, using a radio frequency (RF) transceiver system on the drone-type device, data encoding the measured concentration levels to a ground station.

11. A drone-type device comprising:
a driller configured to penetrate media layers in a subsurface terrain such that the drone-type device travels along a path in the subsurface terrain while searching for a source of one or more pollutants;
one or more sampling compartments configured to hold at least one sample obtained along the path as the drone-type device travels in the subsurface terrain;
one or more sensors on the drone-type device coupled to the one or more sampling compartments, wherein the one or more sensors are configured to measure concentration levels of the one or more pollutants at corresponding locations along the path where the drone-type device obtains the at least one sample;
a processor coupled to the one or more sensors, wherein the processor is configured to perform operations of:
determining a gradient map of the measured concentration levels in the subsurface terrain surrounding the path taken by the drone-type device; and
based on, at least in part, the gradient map, determining whether the source of the one or more pollutants has been located; and
a battery coupled to the driller, the one or more sensors, and the processor.

12. The drone-type device of claim 11, wherein the operation of determining whether the source of the one or more pollutants has been located comprises:
identifying a direction corresponding to an ascending gradient on the determined gradient map; and
steering the drone-type device in the identified direction in the subsurface terrain.

13. The drone-type device of claim 12, wherein the ascending gradient comprises a gradient where the measured concentration level is more elevated than a previously measured concentration level.

14. The drone-type device of claim 12, further comprising:
a ground penetrating radar (GPR) configured to generate a map of the subsurface terrain surrounding where the drone-type device is located, wherein the processor is further configured to perform operations of:
accessing the map of the subsurface terrain; and
based on, at least in part, the map, identifying an underground structure.

15. The drone-type device of claim 14, wherein the processor is further configured to perform operations of:
steering the drone-type device such that the path of the drone-type device does not cross the underground structure.

16. The drone-type device of claim 12, wherein the drone-type device is further configured to:
obtain, using the one or more sampling compartments, at least one additional sample as the drone-type device is steered in the identified direction in the subsurface terrain; and
measure, using the one or more sensors, the concentration levels of the one or more pollutants where the drone-type device obtains the at least one additional sample.

17. The drone-type device of claim 12, wherein the operation of determining whether the source of the one or more pollutants has been located further comprises:
determining that an ascending gradient is absent where the drone-type device is located; and
identifying the source of the one or more pollutants as where the drone-type device is located.

18. The drone-type device of claim 11, wherein the one or more sensors comprise at least one of: a pressure gauge, a thermometer, a PH meter, an oxidation-reduction potential (ORP) sensor, a dissolved oxygen (DO) sensor, or a radiation sensor.

19. The drone-type device of claim 11, further comprising:
a radio frequency (RF) transceiver system configured to communicate data encoding the measured concentration levels to a ground station.

20. The drone-type device of claim 19, wherein the radio frequency (RF) transceiver system is further configured to receive at least one command from ground station such that the one or more sampling compartments are opened according to the at least one command.

\* \* \* \* \*